United States Patent [19]

Advani et al.

[11] 4,399,684
[45] Aug. 23, 1983

[54] GAS MEASUREMENT METHOD

[75] Inventors: Gulu N. Advani, San Jose; Robert Beard, Placerville; Leonard Nanis, Palo Alto, all of Calif.

[73] Assignee: Sierra Monitor Corporation, Sunnyvale, Calif.

[21] Appl. No.: 325,262

[22] Filed: Nov. 27, 1981

[51] Int. Cl.³ .............................................. G01N 27/12
[52] U.S. Cl. ........................................ 73/1 G; 73/23
[58] Field of Search ..................... 73/1 G, 23, 27 R; 340/634; 338/34; 324/71 SN; 422/98

[56] References Cited

U.S. PATENT DOCUMENTS 3,906,473  9/1975  Le Vine ............................... 340/634
4,151,738  5/1979  Hyer et al. ............................ 73/1 G Primary Examiner—Stephen A. Kreitman

[57] ABSTRACT

A gas measurement method for metal-oxide gas sensors. The sensors are thermally cycled by sequential heating and cooling. It has been found that a continuous, concentration-dependent, unique signature for different gases is produced during thermal cycling. Once signature patterns are developed for different concentrations, an unknown gas concentration for which a signature pattern exists may be sampled, either by amplitude or time-dependent samples, in order to identify the gas in its concentration.

5 Claims, 3 Drawing Figures

4,399,684

GAS MEASUREMENT METHOD

DESCRIPTION

1. Technical Field

The invention relates to quantitative gas measurement and in particular quantitative gas measurement using metal oxide sensors.

2. Background Art

Metal oxide gas sensors are described in U.S. Pat. Nos. 3,625,756; 3,631,436; 3,644,795; 3,732,519; 3,835,529; 3,900,815; 3,901,067 and others. These sensors, some of which are invented by N. Taguchi and manufactured by Figaro Engineering Company of Osaka, Japan, contain a gas sensing element which includes a semiconductor material, often in particulate form within a binder, or as a thin film, supported between electrodes. The sensors is usually heated to a constant temperature at which surface oxygen anions become activated, facilitating reaction with gases to be detected. When such reaction occurs, the conductivity of the sensor changes, indicating the presence of gas. Such conductivity changes are measured, yielding a quantitative indication of the amount of reacting gas on the surface of the sensor.

In U.S. Pat. No. 3,906,473 H. Le Vine teaches that Taguchi sensors may be operated alternately and repetitively in a low temperature range for measurements and in a higher temperature range for purging the sensor of adsorbed gases. The sensor is sampled in the lower temperature range to obain gas concentration of carbon monoxide which cannot accurately be measured at the high temperature range because of interferences with other gases.

Notwithstanding the improvement of Le Vine, there are three problems which limit the effectiveness of metal oxide gas sensors. First is the lack of selectively or the inability to distinguish different gases. In the prior art, the indentification of the gas being measured was known or assumed. There is a need for gas sensors having an ability to discriminate among various gases in order to identify a particular gas of interest.

Second is a problem arising from the effects of humidity on the gas sensor. When different levels of humidity are present, prior art gas sensors yield differing output levels for the same gas concentration. Thus water vapor is an interfering gas whose effect cannot be separated from the sample gas.

Third is a problem of gas sensors "falling asleep." A common phenomenon in all solid state sensors is the fact that their response to any gas is dependent on their history of exposure to the gas. Thus, sensors which have been exposed to these gases on a continuous basis alarm rapidly when the gas concentration exceeds a fixed threshold; sensors that have not been exposed to the gases for several days could take very long times to react to their presence at the same concentration that previously caused an alarm.

An object of this invention was to devise a gas measurement method using metal oxide gas sensors which is selective in identifying different gases, as well as identifying varying concentrations of such gases. Another object was to devise a humidity-independent mesurement for such sensors. A further object was to devise a measurement method overcoming the problem of "falling asleep."

DISCLOSURE OF INVENTION

The above objects have been achieved with the discovery that sequential heating and cooling of a gas sensor, i.e. thermal cycling of a sensor, induces a continuous, concentration-dependent, unique signature for different gases. While the entire signature over a thermal cycle yields valuable data, we have found that amplitude or time-dependent samples of the signature yield sufficient information for identifying some gases and their concentrations. In particular, the humidity problem described above may be solved by ratiometric sampling in the following manner. The gas sensor is first calibrated by exposing the sensor to a range of known concentrations of a gas, alone or in a mixture. The sensor is thermally cycled by heating for several seconds and cooling for a similar period. The sensor conductance is measured and recorded at two spaced-apart times in the thermal cycle. Either or both times may be in the heating or cooling intervals. One sampling time may be chosen where humidity effects are minimal. A ratio of the conductances is formed. The sensor is subsequently exposed to an unknown concentration of the same gas and the sensor is thermally cycled in the prescribed manner. A similar measurement is made at the same two times in the thermal cycle. The unknown gas concentration is found by comparing the ratio for the unknown concentration with the previously measured ratios.

In another related method, the time required for a gas to achieve an amplitude level, such as when it reverses its signature amplitude, will characterize the concentration of a gas. Similarly, the amplitude of a signature pattern at a particular time in the signature pattern or the time when it reaches a particular amplitude, will characterize a concentration.

All of these measurement methods rely on measuring selected gas sensor data points in the sensor signature upon thermal cycling, with the benefit of increased selectively, lowering of humidity dependence and elimination of "falling asleep."

BEST MODE FOR CARRYING OUT THE INVENTION

Figure 1:
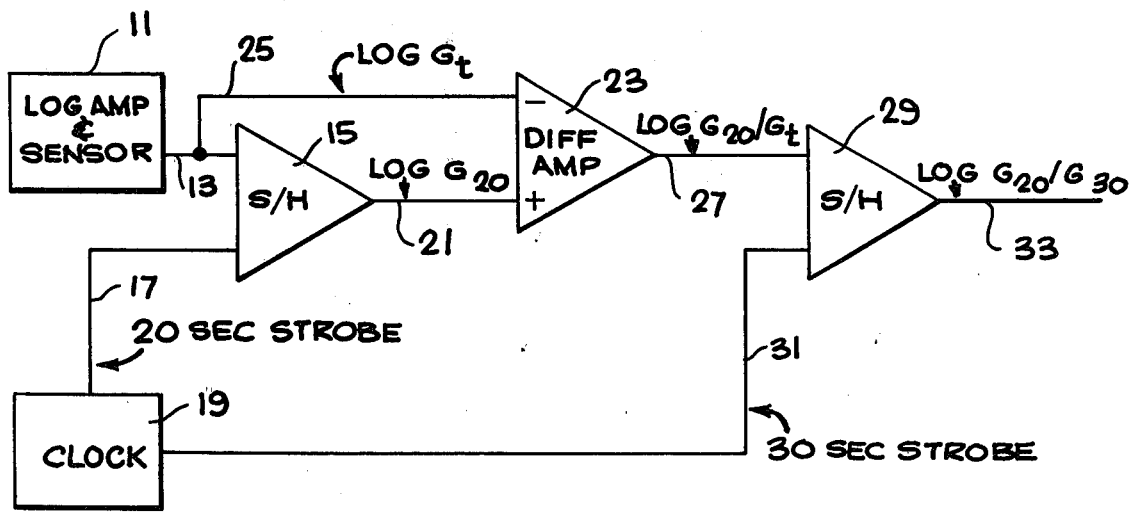
FIG. 1 is an electrical schematic of signal processing electronics for carrying out the method of the present invention.

With reference to FIG. 1 metal-oxide gas sensor 11 is disposed in a manner in which the surface of the sensor comes into contact with a gas being sampled. As mentioned previously, some metal-oxide gas sensors are manufactured by Figaro Engineering Company of Osaka, Japan. The geometric and electrical properties of the sensor are known so that conductivity can be measured directly, such as by means of an electrical meter. A more detailed description of various types of metal-oxide gas sensors is found in the previously mentioned patents.

The sensor 11 is thermally cycled by electrical heating in a known manner. A resistive heater unit is turned on, then later turned off in a repetitive manner. There is no restriction on the heater timing as long as the turnon time is greater than or equal to the time that is required to bring the sensor to a temperature at which oxygen anions are reestablished. Some of these anions are used up a result of reactions with the sample gas. For example, for a Figaro Model 813 sensor, turnon times of 12 to 15 seconds have yielded useful quantitative data. The turnoff time is preferably approximately the same as the turnon time, but may be an order of magnitude, or more, greater. For example, a turnon time of 12 seconds and a turnoff time of 120 seconds has yielded good data. Similarly, equal times of 15 seconds have also yielded useful data. In general, two equal time periods are preferable so that new thermal cycles may be initiated as rapidly as feasible to reduce overall response times.

The gas sensor is connected to a logarithmic amplifier, also indicated by block 11. The output of the log amplifier, a gas signature signal, is transmitted along signal line 13 to a sample-and-hold amplifier 15. This amplifier also has an input along line 17 from a clocking circuit 19 which generates pulses at desired time intervals. These pulses enable the output of sample-and-hold amplifier 15. The clock pulses are referred to as strobes since the duration of the signal is very brief, much less than 1/10 of a second. The period of the strobe transmitted to sample-and-hold circuit 15 establishes the sampling points at spaced-apart times of the thermal cycle.

The output of sample-and-hold circuit 15 is transmitted along line 21 to difference amplifier 23. This signal is the logarithm of the conductance sampled by the strobe and is termed "log $G_{20}$." The signal which is transmitted along line 13 to sample-and-hold circuit 15 is also transmitted to difference amplifier 23 along line 25. This signal is known as "log $G_t$." The difference amplifier 23 produces a signal which is the difference of the logarithms represented by signals on lines 21 and 25. This output signal, taken along line 27 is termed "log $G_{20}/G_t$." This signal is an input to sample-and-hold circuit 29. Another input is a strobe pulse from clock 19, along line 31. The clock signal for this second strobe is different from the time interval for the strobe along line 17. This second strobe, along line 31, defines a second sampling time since the $G_t$ signal becomes fixed by the second strobe. For example, if the second strobe is taken at a 30-second interval, with the 30 seconds being measured from the same starting point as the prior 20-second strobe, the output of sample-and-hold circuit 29, taken along lines 33 will be log $G_{20}/G_{30}$. Assuming that the total period of thermal cycling is 30 seconds, the two strobes provide two sampling intervals during the thermal cycle. Assume that the thermal cycle consists of turning the gas sensor heater off at $t=0$ and turning the heater on 15 seconds later, then turning it off again another 15 seconds later so that the thermal cycle period is 30 seconds. Sampling the gas concentration at $t=20$ seconds is a measurement at one point during the thermal cycle, while sampling at $t=30$ seconds is a measurement at another point in the thermal cycle.

Figure 2:
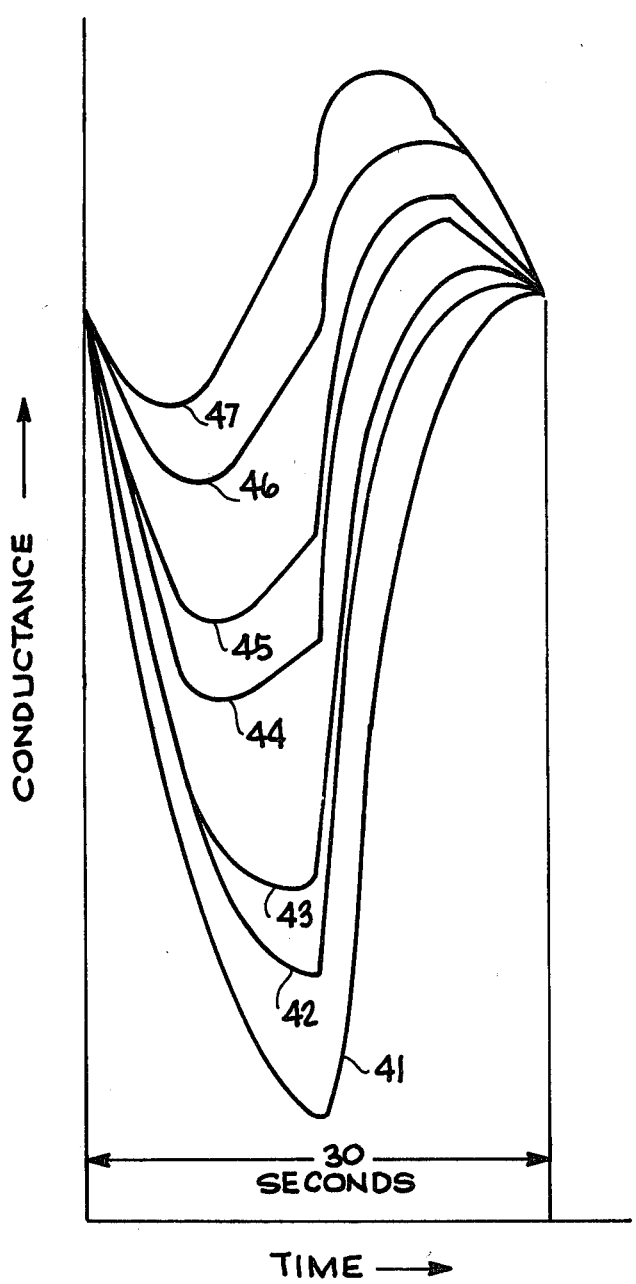
FIG. 2 is a plot of gas concentration signatures over one period of thermal cycling.

FIG. 2 shows characteristic conductance patterns for a thermally cycled metal-oxide gas sensor. The curves of FIG. 2 are ones in which the heater is turned off at $t=0$, and turned on 15 seconds later for a total period of 30 seconds. The data shown is for hydrogen sulfide gas, with conductance measured logarithmically and increasing in the direction indicated by the vertical arrow in the figure. Plot 41 is zero parts per million (ppm). Plot 42 is for 10 ppm; plot 43 for 15 ppm; plot 44 for 33 ppm; plot 45 for 50 ppm; plot 46 for 100 ppm; plot 47 for 1,200 ppm. We have found that for these concentrations of $H_2S$, different characteristic conductance patterns, forming gas signatures, are noted. The same phenomenon can occur for mixtures of gases and is most noticeable when the fraction of one gas in the two-gas system, is held at a constant level.

In this application, sampling of gases has been described in terms of formation of a ratio of conductance at any gas level for two different times. However, from the plot of FIG. 2 it will be seen that other characteristics could be used. For example, FIG. 2 shows that the time to return to a starting level of conductance is an individual characteristic of each gas concentration curve. Similarly, the time that the conductance reaches a peak or a minimal value is slightly different for each curve. These characteristics could also be used to identify gas concentrations.

For these measurements, digital data processing may be used.

Figure 3:
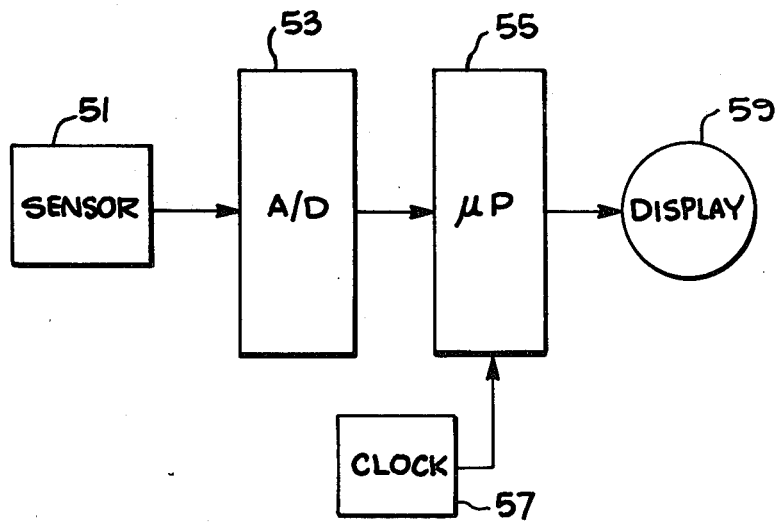
FIG. 3 is an alternate electrical plan for measuring characteristic features of the gas concentration signatures illustrated in FIG. 2.

For example, in FIG. 3 a microprocessor-based data analysis system is shown. A metal-oxide gas sensor 51 produces an analog signal which is converted to a digital signal by analog-to-digital converter 53 and stored in a microprocessor, 55. The microprocessor is clocked by clock 57 for memory refreshing and other purposes. Digital data may then be sampled by microprocessor 55 to detect conductance peaks or valleys, frequency spectrum (using digital filters), conductance ratios, or other conductance pattern recognition techniques, using well-known algorithms. For example, an algorithm for peak detection would involve use of an equation for the derivative of conductance. When the derivative is zero, conductance is at a peak or valley and either can be selected. Once peaks and valleys are determined, the time of occurrence may be measured relative to a point in the thermal cycle, such as the heater turnoff time or $t=0$. Alternatively, other slope detection techniques could be used. As shown from FIG. 2, this data represents a means of identifying a gas concentration level in a unique way. The calibration data may be stored and once a concentration level is identified, it may be shown in the visual display 59.

The gases for which this technique works are all gases which are measurable by metal-oxide gas sensors. One of the benefits of the present invention is that the apparatus of FIG. 1 may be miniaturized in production versions of the invention for use in a portable gas detection instrument.

We claim:

1. A method of operating a metal-oxide semiconductor gas sensor comprising,
    (a.) calibrating a gas sensor by:
        (1) exposing a metal-oxide gas sensor to a range of known gas concentrations, said gas being of a type measurable by the sensor,
        (2) thermally cycling the gas sensor for each gas concentration, the thermal cycle having a heating interval and a cooling interval,
        (3) measuring and recording the ratio of sensor conductance at two times in the thermal cycle, then,
    (b.) mesuring an unknown gas sample by:
        (1) exposing the gas sensor to an unknown concentration of said particular gas while thermally cycling said gas sensor and measuring the ratio of sensor conductance at said two times in the thermal cycle, (2) determining the unknown gas concentration of said particular gas by comparing said ratio measured for the unknown concentration to the previously measured ratios for said gas concentrations in said range of concentrations.

2. A method of operating a metal-oxide semiconductor (MOS) gas sensor comprising,
  (a) calibrating a gas sensor by:
    (1) exposing an MOS gas sensor to a range of known gas concentrations for a particular gas, said gas being of a type measurable by the sensor,
    (2) thermally cycling the gas sensor for each gas concentration, the thermal cycle having a heating interval and a cooling interval,
    (3) measuring and recording conductance characteristics related to each of the heating and cooling intervals in the thermal cycle for gas concentrations in said range of concentrations of said particular gas,
  (b) measuring an unknown gas sample by:
    (1) exposing the MOS gas sensor to an unknown gas concentration of said particular gas while thermally cycling said gas sensor and measuring said conductance characteristic related to intervals in the thermal cycle, and
    (2) determining the unknown gas concentration of said particular gas by comparing the conductance characteristic for the unknown concentration to the previously measured conductance characteristic for said gas concentrations in said range of concentrations.

3. The method of claims 1 or 2 wherein said thermal cycling comprises applying steady power to the sensor for a time in the range of 5 to 60 seconds, then shutting off said power for a time in the range of 5 to 60 seconds.

4. A method of operating a metal-oxide semiconductor gas sensor comprising,
  (a.) calibrating a gas sensor by:
    (1) exposing a metal-oxide gas sensor to a range of known gas concentrations, said gas being of a type measurable by the sensor,
    (2) thermally cycling the gas sensor for each gas concentration, the thermal cycle having a heating interval and a cooling interval,
    (3) measuring and recording the sensor conductance signature pattern at all times in the thermal cycle, then,
  (b.) measuring an unknown gas sample by:
    (1) exposing the gas sensor to an unknown concentration of said particular gas while thermally cycling said gas sensor and measuring the time required to attain a characteristic amplitude in a signature pattern during the thermal cycle,
    (2) determining the unknown gas concentration of said particular gas by comparing said time measured for the unknown concentration to reach a predetermined value to the corresponding time in the previously measured signature pattern for said gas concentrations in said range of concentrations.

5. A method of operating a metal-oxide semiconductor gas sensor comprising,
  (a.) calibrating a gas sensor by:
    (1) exposing a metal-oxide gas sensor to a range of known gas concentrations, said gas being of a type measurable by the sensor,
    (2) thermally cycling the gas sensor for each gas concentration, the thermal cycle having a heating interval and a cooling interval,
    (3) measuring and recording the sensor conductance signature pattern at all times in the thermal cycle, then
  (b.) measuring an unknown gas sample by:
    (1) exposing the gas sensor to an unknown concentration of said particular gas while thermally cycling said gas sensor and measuring the amplitude of a signature pattern at a given time during a thermal cycle,
    (2) determining the unknown gas concentration of said particular gas by comparing said amplitude measured for the unknown concentration at a predetermined time to the corresponding amplitude in the previously measured signature pattern for said gas concentrations in said range of concentrations.

* * * * *